United States Patent [19]

Egan et al.

[11] 4,159,876
[45] Jul. 3, 1979

[54] FLAMELESS ATOMIZATION

[75] Inventors: Edward G. Egan, Mulgrave; Ian S. Jackson, Glen Waverley, both of Australia

[73] Assignee: Varian Techtron Proprietary Limited, Victoria, Australia

[21] Appl. No.: 751,767

[22] Filed: Dec. 16, 1976

[30] Foreign Application Priority Data

Dec. 18, 1975 [AU] Australia ............................... PC4332

[51] Int. Cl.² ............................................. G01J 3/30
[52] U.S. Cl. ................................................. 356/312
[58] Field of Search ................. 356/85, 312; 23/253 R

[56] References Cited
PUBLICATIONS

Lundgren et al., *Analytical Chemistry*, vol. 46, No. 8, Jul. 1974, pp. 1028–1031.
Montaser et al., *Analytical Chemistry*, vol. 47, No. 1, Jan., 1975, pp. 38–45.
Culver et al., *American Laboratory*, vol. 8, No. 3, Mar. 1976, pp. 59–62, 64 and 67–69.

*Primary Examiner*—F. L. Evans
*Attorney, Agent, or Firm*—Stanley Z. Cole; John J. Morrissey; Gerald M. Fisher

[57] ABSTRACT

Chemical analysis apparatus such as a spectrophotometer including an atomizer for receiving a sample to be analyzed and being heated by resistance heating. Control means being provided to vary the voltage across the atomizer, and consequently its temperature, and a feedback circuit is connected between the atomizer and the control means and includes components which are operable to generate an electrical analogue which at least approximates the heating response characteristics of the atomizer. The feedback circuit functions as a negative feedback loop so as to modify the power input to the atomizer by application of the aforementioned electrical analogue, and in that way substantially compensates for the heating response characteristics of the atomizer such that the temperature time profile of the atomizer follows a predictable path.

10 Claims, 6 Drawing Figures

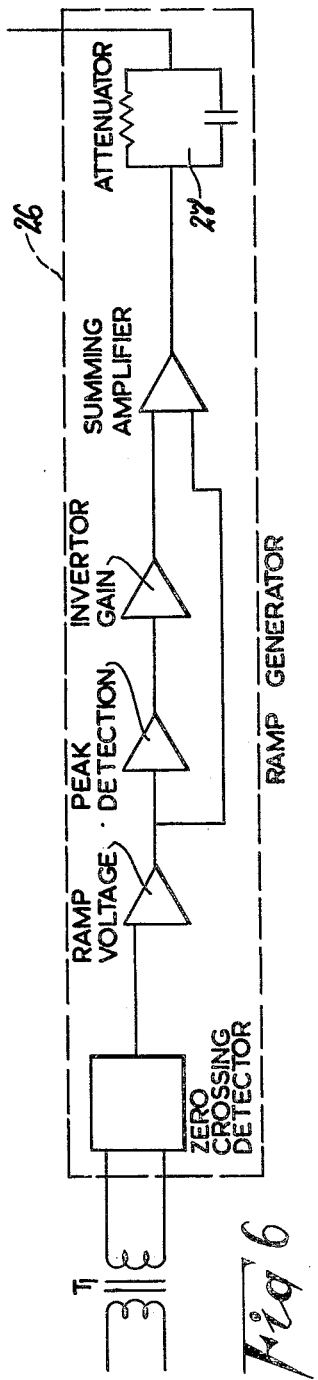
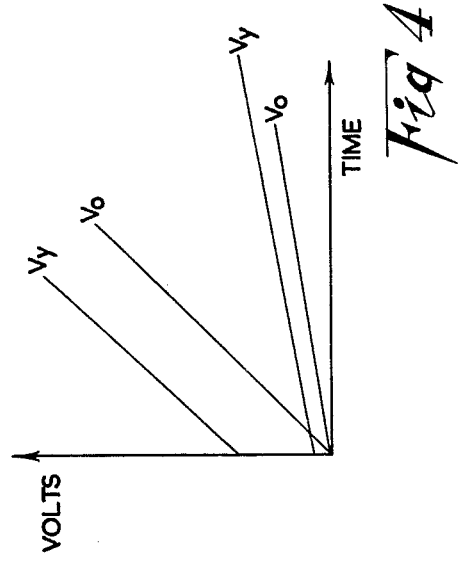
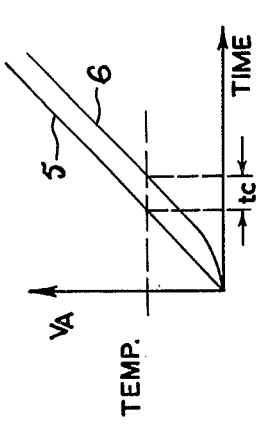
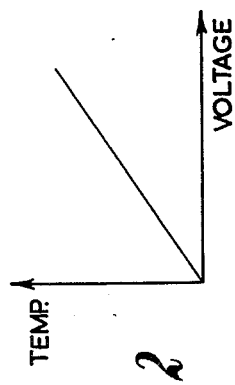
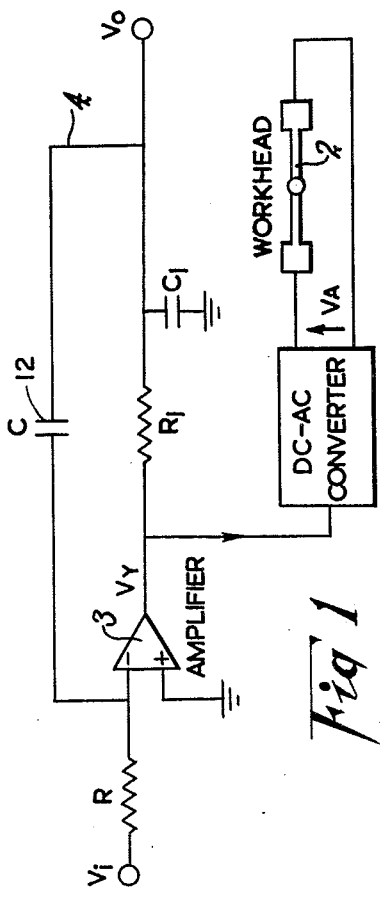

FLAMELESS ATOMIZATION

This invention relates to a method and apparatus for use in flameless atomization of materials, and is especially applicable in chemical analysis equipment such as spectrophotometers, but may have other uses. It will be convenient to hereinafter describe the invention in relation to atomic absorption spectrophotometers.

In atomic absorption spectrophotometers employing flameless atomization, the atomizer is often formed by a carbon element, and the sample to be analyzed is deposited on or within that element usually in the form of a solution. Atomization of the sample in the light path of the instrument results in production of an absorption signal and the peak height or area of the signal is usually taken as a measure of the concentration of the element of interest in the sample solution. Under ideal conditions, the peak height or area of the signal is linearly related to concentration.

During analysis of a sample, the temperature of the atomiser is increased through a range having at its lower level a temperature below that necessary to dry the sample solvent, and at its upper level a temperature sufficient to atomise the sample. In fact, several samples are atomised in turn during the course of a normal analysis program, and the accuracy of the analysis is dependent upon the uniformity of the conditions existing at the atomiser during each atomization step. It is found however, that the temperature conditions of the atomiser vary between the atomization steps, and that variation has an adverse effect on the accuracy of the analysis.

It is a principal object of the invention to provide a method and means whereby the operative conditions of the atomiser can be controlled so as to achieve a temperature profile of a particular form.

In broad terms, the present invention relies on the use of electronic circuitry whereby the atomiser work-head is energized in a controlled manner such as to achieve a temperature-time profile of a particular form, and which form can be reproduced with substantial accuracy in subsequent operations of the atomiser. The temperature-time profile of the work-head is to be understood as equivalent to a physical representation of the temperature variation of the work-head as plotted against time. It is to be further understood that the concept of the invention is applicable in conditions of either rising or falling temperature, although it has its main application in rising temperature conditions (e.g., upwards through the dry, ash and atomising temperature range) and it will be therefore convenient to hereinafter describe the invention with particular reference to that application.

In prior chemical analysis apparatus using non-flame atomisers, the work-head temperature is raised through the aforementioned range by either a stepped or ramped (i.e., linear) increase in the energizing source. For example, the input voltage to the work-head may be stepped or ramped upwards. In either case however, the temperature increase of the work-head lags behind the increase in the degree of energization because of the natural delay in response of the work-head, and furthermore the resulting temperature-time profile is not linear. That response delay and the non-linearity of the temperature-time profile can be conveniently termed the heating response characteristics of the work-head, and because of those characteristics it is difficult to reproduce the same atomising conditions during each atomising step.

According to one aspect of the present invention, there is provided chemical analysis apparatus including;

an atomizer for receiving a sample to be analyzed and being connectable to an electrical power source so as to be heated by resistance heating;

control means operable to vary the power input from said source to said atomizer so as to change the temperature of said atomizer; and a feedback circuit connected between said atomizer and said control means and including means operable to generate an electrical analogue which at least approximates the heating response characteristics of said atomizer;

said circuit being operative to modify said power input by application of said analogue such as to substantially compensate for said heating response characteristics.

According to another aspect of the present invention there is provided a method of controlling temperature changes of an atomizer for use in chemical analysis of a sample, including;

heating said atomizer by electrical resistance heating; and modifying the power input to said atomizer by application of an electrical analogue which at least approximates the heating response characteristics of said atomizer, such that said modification substantially compensates for said heating response characteristics.

It is a feature of the present invention that, when used in a rising temperature situation, the power input to the work-head is caused to rise in a non-linear manner such that the corresponding temperature rise of the work-head follows a particular profile. It is a further feature of the invention that the power input is controlled so as to permit any one of various temperature-time profiles to be achieved, and to also permit substantial reproduction of that profile in subsequent atomising steps. As previously mentioned it will be convenient to particularly describe the invention in relation to a rising temperature situation. It will be also convenient to describe the invention in relation to an arrangement in which the degree of energization of the work-head is varied by changing the input voltage to the work-head, although the desired effect could be achieved in other ways such as by changing the current fed to the work-head.

The following description refers in more detail to these essential features and further optional features of the invention. To facilitate an understanding of the invention, reference is made to the accompanying drawings where these features are illustrated in preferred form. It is to be understood however, that the essential and optional features of the invention are not limited to the specific forms of these features as shown in the drawings.

In the drawings:

FIG. 1 is a schematic circuit diagram of one possible embodiment of the invention;

FIG. 2 is a graph illustrating part of the theory of the invention;

FIGS. 3 and 4 are graphs used in explanation of the theory of the invention;

FIG. 6 is a detailed arrangement of part of the circuit shown in FIG. 5.

Figure 5:
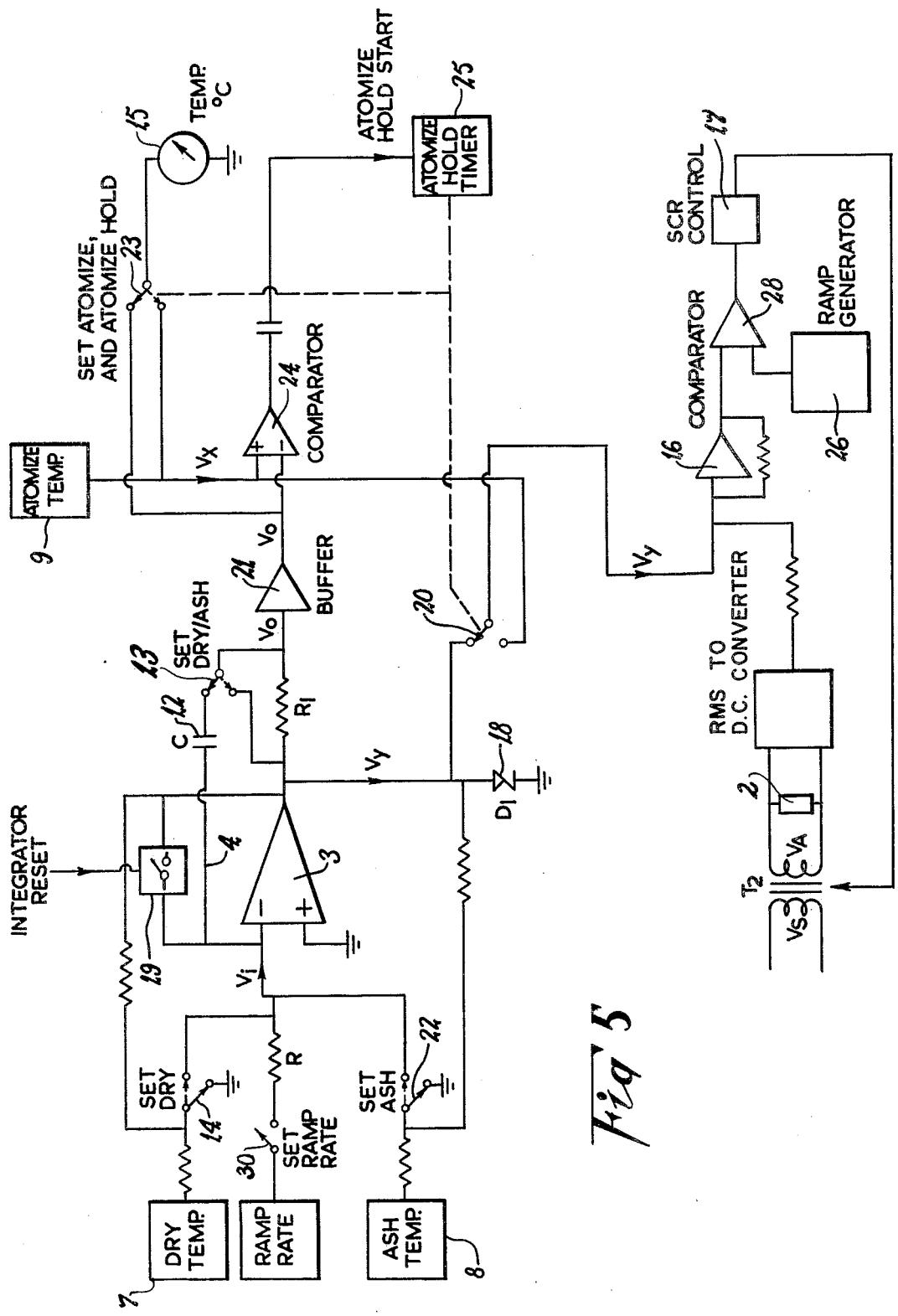
FIG. 5 is a circuit diagram showing the invention as applied to spectrophotometers.

In one particular form of the apparatus, the power supplied to the workhead is modified by varying the input voltage, and that voltage is applied to the workhead through a convertor, and the input voltage to the convertor is influenced by an integrator circuit. The integrator circuit may be of conventional form, and its output is proportional to the input voltage applied to the workhead. A closed negative feed-back loop is connected across the integrator circuit, and that includes components selected to form an electrical analogue of the non-linear heating characteristics of the workhead. Those components preferably include a resistor and a capacitor which are selected to introduce a time constant into the feed-back loop which is substantially equivalent to the temperature response time delay characteristics of the workhead, but it is to be understood that other components could be used to introduce a time constant into the circuit. If desired, one or more of the components may be of variable value to permit adjustment of the circuit to suit changing conditions of use. The actual value of the time constant (or a close approximation thereof) and the necessary characteristics of the circuit components can be determined in a known manner.

A schematic circuit diagram of one possible embodiment of the invention is shown in FIG. 1.

When the example circuit is in use, the input voltage Vi is stepped up to increase the temperature of the workhead 2, and the output from the amplifier 3 is in the form of a decreasing voltage, which would fall on a linear scale but for the presence of the components R1 and C1 in the feed-back loop 4. The output Vo of the circuit will be ramped (i.e., it will fall on a linear scale), and because of the components R1 and C1, the voltage $V_y$ must always assume a value which allows Vo to ramp. If the time constant introduced by R1 and C1 is matched with the temperature-time constant of the workhead 2, the temperature of the workhead 2 will track with Vo and consequently follows a true ramp.

The theory of the invention is based on well known phenomena, as hereinafter explained. If the voltage applied to the workhead in conventional apparatus was suddenly increased, the temperature of the workhead would rise exponentially until a temperature corresponding to the power input was reached. The time taken to reach that temperature will depend upon the heating response characteristics of the particular workhead—e.g., it may be within the range of 1-5 seconds for a spectrophotometer carbon-rod atomizer. If it is assumed that temperature against power input (voltage) can be represented by a line of constant gradient as shown in FIG. 2, the line 5 of the graph of FIG. 3 can be taken as representative of the ideal ramp rate of the workhead temperature as the applied voltage $V_A$ is increased. In actual fact however, the delay characteristics of the workhead causes the temperature to increase in a manner represented by line 6 of FIG. 3, so that the actual workhead temperature lags behind what it should be for the voltage $V_A$ at any particular time.

If $V_A$ is modified by an electrical analogue of the temperature delay characteristics of the workhead 2, it is theoretically possible to compensate for the lag (tc) shown in FIG. 3. If the measured time delay constant of the workhead is 1.8 seconds for example, the components $R_1$ and $C_1$ of FIG. 1 may be selected to introduce a compensating time constant of say 2 seconds.

It has been determined that for $V_o$ to ramp as desired in the circuit described, the drive voltage $V_y$ must ramp at the same rate as $V_o$, but at a value ahead of $V_o$. That value will increase as the ramp rate increases, as is represented by the graph of FIG. 4 which shows the difference between $V_y$ and $V_o$ at two different ramp rates.

FIG. 5 shows a more detailed form of the general circuit shown in FIG. 1, and which is an example of a circuit for use in a spectrophotometer. In that circuit, potentiometers 7, 8 and 9, or other suitable means, are provided to enable selection of the desired dry, ash, and atomise temperatures respectively. An integrator circuit including an amplifier 3 and capacitor 12 is operable, when switch 13 is in the position shown in broken line, to function as an inverting amplifier for the purpose of temperature setting. If the dry temperature, for example, is to be set, switch 14 is moved to the position shown in broken line, and the selected temperature is observable at meter 15.

When the spectrophotometer is to be operated in the dry mode, switch 14 remains as for temperature setting, switch 13 is moved to the position shown in broken line, and switch 20 is in the position shown in full line. The integrator circuit then functions in a normal manner. Resistance $R_1$ and capacitor 12 cooperate to introduce the compensating time constant as previously discussed, and voltage $V_o$ follows the actual temperature of the workhead 2 because of the time delay compensation, and consequently an accurate read-out of workhead temperature is available at meter 15. The voltage $V_A$ applied to the workhead 2 is maintained at an appropriate level through a feed-back circuit including amplifier 16 which compares a DC equivalent of the RMS value of $V_A$ with the compensated drive voltage $V_y$, and an S.C.R. control 17 which is triggered according to the detected differences between $V_A$ and $V_y$ such that $V_A$ is modified as required to cause appropriate heating of the workhead 2. That voltage regulation aspect is more fully described in co-pending U.S. application Ser. No. 751,761, and the disclosure of the specification of that application is to be understood as imported herein by reference.

Diode 18 functions to limit the drive voltage to that which corresponds to the maximum possible temperature of the workhead, and suitable means 19 is provided to cause discharge of the capacitor 12 and thereby permit resetting of the integrator circuit when required. A buffer amplifier 21 serves to guard against loading of the integrator circuit by the remainder of the circuit shown.

Selection of the ash temperature and operation in the ash mode is as described above in relation to the dry temperature, except that switch 22 is actuated in place of switch 14.

The atomize temperature is set by potentiometer 9, and the switch 23 is moved to the position shown by the broken line. When the atomize mode of operation is adopted, switch 13 is moved to the full line position, switches 14 and 22 are in their full line positions and the set ramp rate switch 30 is closed. It is usual, to arrange the circuit so that the drive voltage $V_y$ is made to saturate (i.e., it levels out) at a voltage corresponding to the maximum temperature possible, and at that time $V_o$ ceases to ramp and becomes exponential such as to match the actual temperature of the workhead 2. Since the output $V_o$ is fed to the read-out meter 15 and is characteristic of the actual workhead temperature, a substantially accurate read-out is achieved. That is, actual temperature changes of the workhead 2 are followed by the meter 15, or any other alternative read-out instrument as may be used.

When the voltage $V_X$ is reached, the comparator 24 functions to energise a timer switch 25 which in turn causes movement of the switches 23 and 20 to the broken line positions. Under those conditions, the feedback circuit including $R_1$ and capacitor 12 is disconnected, and the maximum temperature which corresponds to voltage $V_X$ is held for a suitable period of time.

In the example circuit of FIGS. 5 and 6, it is preferred that the electrical resistance of the atomizer heater circuit is arranged so that the electrical resistance of the atomizer 2 is substantially matched with the resistance of the remainder of that circuit. In particular, it is preferred that the atomizer resistance is related to the resistance of the remainder of the circuit so that operational variations of the atomizer resistance do not substantially affect power dissipation in the atomizer during heating. The aspect is more fully described in the aforementioned patent application Ser. No. 751,761.

Furthermore, the feed-back circuit by which the DC voltage equivalent to voltages $V_A$ and $V_y$ are compared and $V_A$ is modified as required, may also function as described in the aforementioned Australian application. In brief, that circuit involves a ramp generator 26 which generates a voltage output of saw-tooth wave form which is synchronized with the mains current, and the general components of the generator 26 are shown in FIG. 6. As explained in the aforementioned patent application Ser. No. 751,761, the attenuator 27 functions to distort the peak of the output signal to provide a narrow region above that peak such as to ensure full drive conduction of the generator 26 when the difference between the DC voltage equivalent to $V_A$ and $V_y$ is at a maxium.

Summing amplifier 16 functions to generate an error signal characteristic of the difference between the DC voltage equivalent to $V_A$ and $V_y$, and that error signal is compared with the output of the generator 26 by comparator 28. The output of the comparator 28 is a pulsed signal, which is naturally characteristic of the aforementioned difference, and that signal is used to trigger the S.C.R. control 17 which in turn functions to modify $V_A$ as necessary to achieve the desired workhead temperature.

The particular arrangement described above aims to achieve a substantially linear increase in workhead temperature, but it may be that some other form of temperature-time profile will be found more suitable in particular circumstances. In the arrangement described, a non-linear profile could be obtained by varying the input voltage Vi in a controlled and reproducible manner, whilst retaining the electrical analogue of the workhead temperature-time characteristics as provided by the components $R_1$ and $C_1$, or other circuit components as might be used for that purpose.

It will be understood from the foregoing that the invention resides in use of an electrical circuit which simulates the temperature-time characteristics of the workhead and modifies the energization source of the workhead such as to permit control of the workhead temperature-time profile. In the example circuit particularly described, a C-R network is utilized to introduce a time constant which is calculated to optimize the performance of the associated apparatus in a particular workhead temperature range, but that time constant could be variable or programmable in other circumstances. Also, as previously stated, an entirely different circuit might be used to achieve the desired results.

By using the aforementioned simulation in a suitable circuit, it is possible to program any desired temperature-time performance. The particular case described utilizes a feed-back circuit to generate a ramped temperature-time profile, but it is important to understand that the concept can be used to give any desired profile which may prove to be useful.

Finally it is to be understood that various alterations, modifications and/or additions may be introduced into the constructions and arrangements of parts previously described without departing from the spirit or ambit of the invention as defined by the appended claims.

Having now described our invention, what we claim as new and desire to secure by Letters Patent is:

1. Chemical analysis apparatus including;
   an atomizer for receiving a sample to be analyzed and being connectable to an electrical power source so as to be heated by resistance heating;
   control means operable to vary the power input from said source to said atomizer so as to change the temperature of said atomizer; and
   a feedback circuit connected between said atomizer and said control means and including means operable to generate an electrical analogue which at least approximates heating response characteristics of said atomizer;
   said circuit being operative to modify said power input by application of said analogue such as to substantially compensate for said heating response characteristics.

2. Apparatus according to claim 1, wherein a convertor is provided to vary said power input by varying the voltage applied across said atomizer, an integrator circuit is connected to said convertor and is operable to influence the input voltage to said convertor, and said feedback circuit comprises a closed negative feedback loop connected across the integrator circuit, said feedback loop including components selected to form said electrical analogue.

3. Apparatus according to claim 2, wherein said components selected to form said electrical analogue includes a resistor and a capacitor which are selected to introduce a time constant into the feedback loop which is substantially equivalent to the temperature response time delay of the heating response characteristics of the atomizer.

4. Apparatus according to claim 1, wherein said atomizer is included in a heater circuit, the total electrical resistance of which is the sum of the atomizer resistance and a further resistance which is the electrical resistance of that part of said circuit other than said atomizer, and said further resistance is preselected relative to said atomizer resistance such that operational variations of said atomizer resistance do not substantially affect power dissipation in said atomizer during heating thereof.

5. Apparatus according to claim 4, wherein said further resistance is no less than half and no more than twice said atomizer resistance.

6. Apparatus according to claim 4 wherein said further resistance is formed at least in part by the inherent resistance of the electrical circuit to which said power source is connected to said atomizer, and is in series with said atomizer.

7. Apparatus according to claim 4, wherein a further feedback circuit is connected to said power source and is operative to modify the voltage applied to said atomizer in accordance with detected differences between that voltage and said modified power input.

8. In a spectrophotometer, an atomizer for receiving a sample to be analyzed and connectable to an electrical power source to be heated by resistance heating;
   control means operable to vary the power input to said atomizer so as to change the temperature of said atomizer, and including means for selecting temperatures suitable for dry-ash, and atomized modes of operation; and
   a feedback circuit connected between said atomizer and said control means and including means operable to generate an electrical analogue which at least approximates the heating response characteristics of said atomizer;
   said circuit being operative to modify said power input by application of said analogue such as to substantially compensate for said heating response characteristics.

9. In a spectrophotometer as defined in claim 8, timer means operative to disconnect said feedback circuit when said temperature is at a preselected maximum atomized temperature.

10. A method of controlling temperature changes of an atomizer for use in chemical analysis of a sample, including;
   heating said atomizer by electrical resistance heating; and
   modifying the power input to said atomizer by application of an electrical analogue which at least approximates the heating response characteristics of said atomizer, such that said modification substantially compensates for said heating response characteristics.

* * * * *